United States Patent [19]

Adelstein et al.

[11] 4,025,524

[45] May 24, 1977

[54] 2-{3-[4-AZATRICYCLO(4.3.1.1$^{3,8}$)UNDECAN-4-YL]-1,1-DIPHENYLPROPYL}-5-METHYL-1,3,4-OXADIAZOLE AND CONGENERS

[75] Inventors: Gilbert W. Adelstein, Evanston; H. William Sause, Deerfield, both of Ill.

[73] Assignee: G. D. Searle & Co., Chicago, Ill.

[22] Filed: Jan. 26, 1976

[21] Appl. No.: 652,361

Related U.S. Application Data

[63] Continuation-in-part of Ser. No. 568,405, April 16, 1975, abandoned.

[52] U.S. Cl. ............................ 260/296 R; 424/263; 424/272; 260/239 B; 260/307 E; 260/308 D
[51] Int. Cl.$^2$ ........................................ C07D 413/02
[58] Field of Search ..................... 260/307 G, 296 R

[56] References Cited

UNITED STATES PATENTS 3,444,180  5/1969  Maeder et al. ................ 260/307 G

OTHER PUBLICATIONS

B568,405, Mar. 1976, Adelstein et al., 260/307 G.

*Primary Examiner*—John D. Randolph
*Attorney, Agent, or Firm*—John M. Brown

[57] ABSTRACT

Preparation and the valuable antispasmodic, antiarrhythmic, antidiarrheal, and antiviral properties of 2-{3-[4-azatricyclo(4.3.1.1$^{3,8}$)undecan-4-yl]-1,1-diphenylpropyl}-5-methyl-1,3,4-oxadiazole and congeners are disclosed.

5 Claims, No Drawings

2-{3-[4-AZATRICYCLO(4.3.1.1^{3,8})UNDECAN-4-YL]-1,1-DIPHENYLPROPYL}-5-METHYL-1,3,4-OXADIAZOLE AND CONGENERS

The application for Letters Patent securing the invention herein described and claimed is a continuation-in-part of applicants' copending application Ser. No. 568,405 filed Apr. 16, 1975 and now abandoned.

This invention relates to 2-{3-[4-azatricyclo(4.3.1.1.$^{3,8}$)undecan-4-yl]-1,1-diphenylpropyl}-5-methyl-1,3,4-oxadiazole and congeners, and to processes for the preparation thereof. More particularly, this invention provides new, useful, and unobvious chemical compounds of the formula

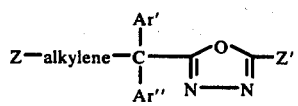

wherein Z represents 4-azatricyclo[4.3.1.1$^{3,8}$]undecan-4-yl; Ar' and Ar'' each represent phenyl optionally substituted by alkyl, halogen, and/or alkoxy; and Z' represents hydrogen or alkyl. Alternatively, Ar' represents 2-, 3-, or 4- pyridinyl.

From 1 to as many as 10 of the aforesaid optional substituents, alike or different, can be present in the carbocyclic groupings represented by Ar' and Ar'', the positioning of the substituent(s) both with respect to each other (when more than one is present) and to the points of attachment of the groupings to the remainder of the enformulated molecules being acritical.

Among the alkyls contemplated by Ar', Ar'', and Z', lower alkyls are preferred, which is to say methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain, hydrocarbon groupings of empirical formula

wherein n represents a positive integer less than 8. The alkoxys contemplated by Ar' and Ar'' likewise are preferably of lower order, and thus may be represented by the formula

wherein "lower alkyl" is defined as above. The halogens contemplated by Ar' and Ar'' are fluorine, chlorine, bromine, and iodine; and, finally, the alkylene called for in the introductory and generic formula preferably comprises at least 2 carbons, as for example 1,2-ethanediyl, 1-methyl-1,2-ethanediyl, 1,1-dimethyl-1,2-ethanediyl, ,3-propanediyl, 2,2-dimethyl-1,3-propanediyl, 1,4-butanediyl, and like bivalent, saturated, acyclic, straight- or branched-chained hydrocarbon groupings of empirical formula

wherein m represents a positive integer greater than 1 and less than 6.

Equivalent to the foregoing compounds for the purposes of this invention are non-toxic acid addition salts thereof having the formula

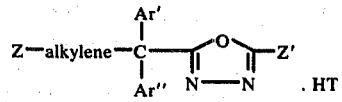

wherein Z, Z', Ar', and Ar'' are defined as before and T represents 1 equivalent of an anion - for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like - which, in combination with the cationic portion of a salt aforesaid, is neither biologically nor otherwise incompatible.

The compounds to which this invention relates are useful by reason of their valuable biological properties. Thus, for example, they are antispasmodic, antiarrhythmic, antidiarrheal, and - vis-a-vis at least myxoviruses of which Influenza A (Strain 575) is typical - antiviral.

The antispasmodic utility of the instant compounds can be demonstrated via a standardized test for their capacity to antagonize the activity of bradykinin, prostaglandin $E_2$ ($PGE_2$) and/or acetylcholine. The procedure, carried out substantially as described by J. H. Sanner in Arch. intern. Pharmacodynamie, 180, 46 (1969), is as follows: A female guinea pig weighing between 200 and 500 g is sacrificed by cervical dislocation, whereupon the ileum is quickly removed and a 2-cm segment thereof mounted in a 5-ml tissue bath containing modified Tyrode solution and adapted to record isotonic contractions. The Tyrode solution, at 37° C and constantly bubbled with a mixture of 95% oxygen and 5% carbon dioxide (V/V), consists of 8.046 g of NaCl, 0.200 g of KCL, 0.132 g of $CaCl_2.2H_2O$, 0.107 g of $MgCl_2.6H_2O$, 1.000 g of $NaHCO_3$, 0.058 g of $NaH_2PO_4.H_2O$, 1.000 g of dextrose, and water q.s. 1 l. Doses of bradykinin, $PGE_2$, and acetylcholine necessary to induce approximately equal submaximal contractions are experimentally determined, whereupon two sets of three (one for each agonist at the predetermined dose) such contractions are recorded at 4-minute intervals as controls. The modified Tyrode solution is immediately replaced by a solution or suspension of test compound therein, at 37° C and bubbled as before, following which three sets of contractions induced by the three agonists at the predetermined doses are recorded, beginning 4 minutes after the second control recording and continuing at 4-minutes intervals thereafter. The first of these three sets serves only to maintain the dosage timing until the tissue is in equilibrium with the test compound. The last two sets are compared with the two control sets, and a compound is considered active vis-a-vis a given agonist if the mean contraction induced thereby in the presence control contraction for that agonist. The initial screening dose in this test is ordinarily 30 mcg per ml, at which dose the product of Example 1F hereinafter reduced the spasmodic effects of bradykinin and $PGE_2$ by 95% and 93% respectively, and totally blocked the effect of acetylcholine. The product of Example 6D hereinafter reduced the spasmodic effects of $PGE_2$ and acetylcholine by 91% and 97%, respectively, at the 30 mcgm per ml dose level.

The antiarrhythmic utility of the instant compounds can be demonstrated by a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. Composition of the perfusion solution is the same as Lucchesi's, but the volume is increased to 211 ml and the temperature lowered to 28° C. Aconitine (ordinarily as the nitrate) is administered as soon as the heart beat is regular and the EKG pattern normal, the dose being so selected as to at least double the rate. Typically, 0.05 ml of 0.1% aconitine nitrate in physiological saline is injected. EKG's are recorded at 5-minute intervals after onset of ventricular tachycardia until two successive readings show stabilization of the rate. Perfusate collected during this time is discarded and replaced with fresh solution q.s. 200 ml. Promptly following stabilization, 2mg of compound dissolved or suspended in 1 ml of physiological saline is mixed wih the perfusion solution; 10 minutes later a like amount is introduced, followed after a further 10 minutes by double the first amount. Final concentration of compound in the perfusion solution is thus 40 mg per 1. Recording of EKG's is continued at 5-minute intervals throughout this time and for 10 minutes thereafter. A compound is considered antiarrhythmic if, at any time during the 30 minutes immediately following initial administration in more than half of a minimum of 2 tests, it reduces by at least 50% the rate recorded 10 minutes after onset of tachycardia. The products of Example 1F and 2D hereinafter were antiarrhythmic in this test.

The antiaarhythmic utility of the instant compounds can be further demonstrated via a standardized test for their capacity to counteract the ventricular ectopic arrhythmia induced by a 2-stage ligation of the anterior descending branch of the left coronary artery in the intact dog. The ligation technique, performed substantially as described by A. Sidney Harris in Circulation, 1, 1318 (1950), involves anesthetizing the animal with 32.5 mg per kg of sodium pentobarbital, administered intravenously, and maintaining respiration mechanically via tracheal intubation while the chest cavity is opened on the left side at the fourth interspace and (1) the artery is tied against a 20-gage hypodermic needle at a point approximately 1 cm from the atrial tip, (2) the needle is removed, (3) 30 minutes later the artery is completely occluded by ligation, and (4) the opening is closed. On the first post-operative day, if an EKG reveals $\not> 75\%$ ectopic beats, 5 mg per kg of compound dissolved or suspended at a concentration of 1% in aqueous 0.9% sodium chloride or other physiologically inert vehicle is administered during 5 minutes via a scalp-vein needle placed in the cephalic vein. EKG's are recorded at 2.5-minute intervals until there is either a reduction in ectopic beats amounting to at least 25% and lasting for a minimum of 10 minutes or a total drug dose of 20 mg per kg has been administered. A compound is considered antiaarhythmic in this test if the aforesaid reduction is induced in more than half of at least 2 dogs. The product of Example 1F hereinafter was antiarrhythmic at 5 mg per kg in this test.

The antiarrhythmic utility of the instant compounds can be still further demonstrated via a standardized test for their capacity to restore normal sinus rhythm in dogs pretreated with sufficient ouabain to induce ventricular tachycardia. The test animals are anesthetized with 37.5 mg per kg of sodium pentobarbital; an endotracheal tube is emplaced to facilitate breathing; Lead II EKG's are monitored; and drugs are introduced via a cannula in the left femoral vein, each dose being washed in with 1 ml of a 0.1% solution of heparin in aqueous 0.9% sodium chloride. Heart beats per minute are calculated by multiplying the number of QRS patterns during a 6-second period by 10.Initially, a 40-mcgm-per-kg dose of the ouabain solution is administered after 30 minutes if the heart beat remains normal, or after 45 minutes if arrhythmic at the 30-minute mark but normal 15 minutes later. A still further 0-mcgm-per-kg dose of the ouabain solution is administered 15 minutes after the 20-mcgm-per-kg dose if the heart beat is normal, or 30 minutes after the 20-mcgm-per-kg dose if arrhythmia 15 minutes thereafter has reverted to normal. Additional 10-mcgm-per-kg doses of the ouabain solution are administered at 15-or-30-minute intervals as above if necessary, the total ouabain dosage being the minimum amount necessary to induce ventricular tachycardia which is self-sustaining for at least 15 minutes. To such animals, the compound to be tested is administered in a vehicle consisting of aqueous 0.9% sodium chloride, $\not> 95\%$ propylene glycol, or other physiologically inert vehicle at a concentration of 1%. The initial dose of compound is ordinarily 5 mg per kg. A compound is considered antiarrhythmic in this test if it restores normal sinus rhythm persisting for 15 minutes in more than half of a minimum of 2 animals at a dose of 20 mg per kg or less. Doses larger than 5 mg per kg are ordinarily administered in 5-mg-per-kg increments spaced approximately 15 minutes apart. The product of Example 1F hereinafter was antiarrhythmic at 5 mg per kg in this test.

The antidiarrheal utility of the instant compounds can be demonstrated by the following standardized test for their capacity to induce constipation in mice. To each of a group of 6 male Charles River mice weighing 20–25 g and fasted for the 24 hours immediately preceding, a suspension of compound in 10 ml per kg of vehicle (ordinarily ½% aqueous methyl cellulose), followed ½ hour later by 0.2 ml of a 10% charcoal suspension in aqueous 1% methyl cellulose, is administered. Compound is administered either intragastrically or subcutaneously (ordinarily at 3 dose levels, such as 100, 30, and 10 mg per kg); the charcoal suspension is administered intragastrically. Controls are provided by substituting 10 ml per kg of vehicle sans compound in the foregoing procedure. The mice are sacrificed by cervical dislocation 3½ hr. after administration of the charcoal suspension, and their ceca are examined for the presence of any charcoal. Plotting the numbers of mice in which no charcoal is present (indicating activity) against the doses of compound administered affords a dose-response curve from which the $ED_{50}$ for the compound can be calculated by such statistical methods as that of J. Berkson [J. Amer. Statist. Assoc., 48, 565 (1953)]. The antidiarrheal $ED_{50}$ of the product of Example 1F hereinafter was approximately 5 mg per kg in this test.

The antidiarrheal utility of the instant compounds can be further demonstrated via a standardized test for their capacity to counteract the diarrheic effect of castor oil in rats. The procedure, modeled after that of Niemegeers et al., Arzneimittel-Forsch., 22, 516 (1972), is as follows: To each of a group of 12 adult Charles River rats weighing 180-200 g and fasted - but with free access to water - in community cages for the 24 hours immediately preceding, is intragastrically administered a suspension of compound (ordinarily at 3 dose levels, such as 100, 30, and 10 mg per kg) in 10 ml per kg of vehicle (ordinarily ½% aqueous methyl cellulose), followed 1 hour later by 1 ml of castor oil. Controls are provided by substituting 10 ml per kg of vehicle sans compound in the foregoing procedure. Hourly during a maximum of 8 hours immediately following administration of castor oil, the rats are observed for evidence of diarrhea. Plotting the number of rats in which diarrhea is not evident after a given time against the doses of compound administered affords a dose-response curve from which the $ED_{50}$ for the compound at the selected time can be calculated by such statistical methods as that of Berkson et al., loc. cit. The antidiarrheal $ED_{50}$ of the product of Example 1F hereinafter 8 hr. after administration of castor oil in this test was approximately 11 mg per kg.

The antiviral utility of the instant compounds can be demonstrated via the standardized test described in U.S. Pat. No. 3,845,038, column 3, lines 19–55. The product of Example 1F hereinafter was antiviral at a concentration of 25 mcgm per ml in that test.

The foregoing test results are provided by way of illustration, and not as delimiting. Those skilled in the art will recognize that observations of activity in standardized tests for particular biological effects are fundamental to the development of valuable new drugs, both veterinary and human.

Preparation of compounds of this invention proceeds by heating an amino alkyl halide of the formula

with the sodio derivative of a nitrile of the formula

obtained by heating the nitrile with a 5% dispersion of sodium hydride under nitrogen, using toluene as the reaction medium. The resultant aminoalkanenitrile

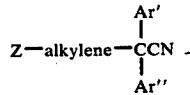

is heated with sodium azide in the presence of ammonium chloride and lithium chloride, using N,N-dimethylformamide as the reaction medium. Heating the resulting tetrazole

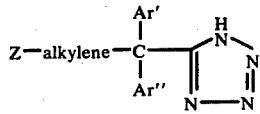

in pyridine with an anhydride of the formula

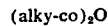

affords a 1,3,4-oxadiazole of this invention having the formula

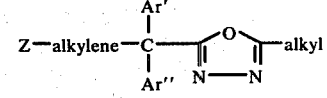

whereas heating the tetrazole with ethyl oxalyl chloride in pyridine under nitrogen affords a 1,3,4-oxadiazole-2-carboxylic acid ethyl ester of the formula

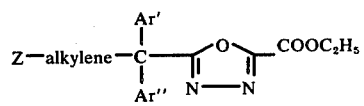

from which, by saponifying the ester linkage therein with hot aqueous sodium hydroxide and heating the resultant carboxylic acid at temperatures just sufficiently high to effect decarboxylation, a 1,3,4-oxadiazole of the invention having the formula

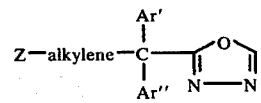

is obtained. Conversion of a base of this invention to an equivalent acid addition salt is accomplished by simple admixture with 1 equivalent of any of various inorganic and strong organic acids, the anionic portion of which conforms to T as hereinbefore defined. Throughout the foregoing formulas, Z,Ar', and Ar" retain the meanings originally assigned.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 18 parts of α-phenylbenzeneacetonitrile in 140 parts of dry toluene is added, with stirring under nitrogen, approximately 4 parts of a 57% dispersion of sodium hydride in oil. The resultant mixture is heated to 90° and stirred thereat under nitrogen for ¾ hr. The yellow-green flocculent suspension which eventuates is cooled to around 65°, whereupon 20 parts of 4-(2-chloroethyl)-4-azatricyclo[4.3.1.1$^{3,8}$]undecane [preparable by mixing the hydrochloride thereof (U.S. Pat. No. 3,845,038) with excess aqueous sodium carbonate, extracting the mixture with toluene, and consecutively washing the extract with water, drying it over anhydrous sodium sulfate, filtering out the drying agent, and removing the solvent by vacuum distillation] in 85 parts of dry toluene is introduced, with stirring, during 15 minutes. The mixture thus obtained is stirred for 2 hours at 90°–100°. The yellow-orange solution which results is cooled to room temperature, at which point 20 parts of water is stirred in. Aqueous and organic phases are separated, the aqueous phase is extracted with toluene and then discarded, and the extract and organic phases are combined and thereupon consecutively washed with water, dried over anhydrous sodium sulfate, and filtered. The filtrate is stripped of solvent by vacuum distillation, affording 4-[4-azatricyclo(4.2,1.1$^{3,8}$)undecan-4-yl]-2,2-diphenylbutanenitrile as the residue. The product has the formula

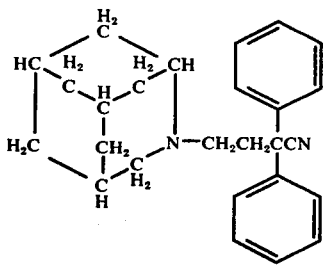

B. A solution of 1 part of 4-[4-azatricyclo(4.3.1.1$^{3,8}$)undecan-4-yl]-2,2-diphenylbutanenitrile in a minimal amount of diethyl ether is acidified with a solution of hydrogen chloride in 2-propanol. The precipitate which forms is filtered off and recrystallized from water containing a trace of hydrochloric acid. The product thus isolated is 4-[4-azatricyclo(4.3.1.1$^{3,8}$)-undecan-4-yl]-2,2-diphenylbutanenitrile hydrochloride melting at 78°-80°.

C. A mixture of approximately 242 parts of 4-[4-azatricyclo(4.3.1.1$^{3,8}$)undecan-4-yl]-2,2-diphenylbutanenitrile hydrochloride, 65 parts of sodium azide, 53 parts of ammonium chloride, 1 part of lithium chloride, and 1140 parts of N,N-dimethylformamide is stirred at 110°-125° for 9 hours, then chilled. The precipitate which forms is filtered off, consecutively washed with N,N-dimethylformamide and water, then dried in air. The product thus isolated is 5-{3-[4-azatricyclo(4.3.1.1$^{3,8}$)-undecan-4-yl]-1,1-diphenylpropyl}-1H-tetrazole melting at 262°-263° with gas evolution. It has the formula

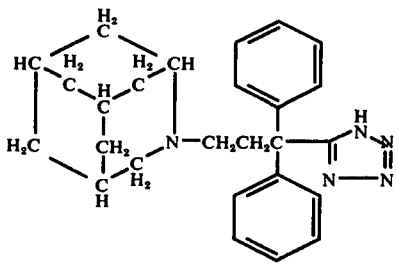

D. A solution of 1 part of 5-{3-[4-azatricyclo(4.3.1.1$^{3,8}$)undecan-4-yl]-1,1-diphenylpropyl}-1H-tetrazole in 10 parts of aqueous 1% sodium hydroxide is acidified with dilute hydrochloric acid. The precipitate which forms is filtered off, washed with water, and dried in air. The product thus isolated is a hydrate of 5-{3-[4-azatricyclo(4.3.1.1$^{3,8}$)undecan-4-yl]-1,1-diphenylpropyl}-1H-tetrazole hydrochloride containing ⅔ of a mole of water per mole of salt. The water of crystallization can be removed by heating in vacuo.

E. A solution of 48 parts of 5-{3-[4-azatricyclo(4.3.1.1$^{3,8}$)undecan-4-yl]-1,1-diphenylpropyl}-1H-tetrazole and 140 parts of acetic anhydride in 400 parts of pyridine is heated at the boiling point under reflux for 3 hours, then cooled and thereupon diluted with 100 parts of water. The resultant mixture is stirred for 10 minutes, whereupon solvent is removed by vacuum distillation and the residue partitioned between a saturated aqueous solution of sodium bicarbonate and diethyl ether. The ethereal phase is separated and consecutively washed with a saturated aqueous solution of sodium bicarbonate and water, then extracted with 2% hydrochloric acid. The acid extract is made alkaline, and the resultant mixture is extracted with ether. The ether extract is washed with water, dried over anhydrous sodium sulfate, and filtered. The filtrate, stripped of solvent by vacuum distillation, affords 2-{3-[4-azatricyclo(4.3.1.1$^{3,8}$)undecan-4-yl]-1,1-diphenylpropyl}-5-methyl-1,3,4-oxadiazole melting at approximately 120°-121° as the residue. It has the formula

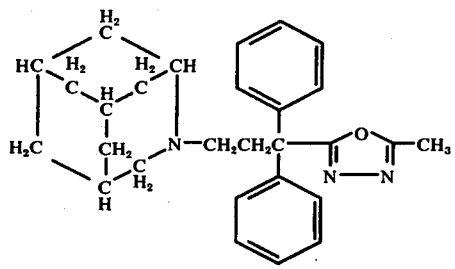

F. A solution of 1 part of 2-{3-[4-azatricyclo(4.3.1.1$^{3,8}$)undecan-4-yl]-1,1-diphenylpropyl}-5-methyl1,3,4-oxadiazole in 20 parts of diethyl ether is acidified with a solution of hydrogen chloride in 2-propanol. The precipitate which forms is isolated by filtration and dried in air. The product thus obtained is 2-{3-[4-azatricyclo(4.3.1.1$^{3,8}$)undecan-4-yl]-1,1-diphenylpropyl}-5-methyl-1,3,4-oxadiazone hydrochloride.

EXAMPLE 2

A. A solution of 13 parts of α-phenylbenzeneacetonitrile in 70 parts of dry toluene is stirred and heated at 80° under nitrogen with approximately 3 parts of sodamide until a yellow-brown flocculent suspension develops, whereupon a solution of approximately 15 parts of 4-(2-chloropropyl)-4-azatricyclo[4.3.1.1$^{3,8}$]undecane [preparable from the hydrochloride (U.S. Pat. No. 3,845,035) as described in Example 1A herein] in 70 parts of dry toluene is stirred in during ½ hour. The mixture thus obtained is stirred under nitrogen at 90° for 4½ hours, at which point the mixture is cooled and then diluted with 10 parts of water. The organic phase is separated, washed to the point of neutrality with water, dried over anhydrous sodium sulfate, and filtered. The filtrate, stripped of solvent by vacuum distillation, affords a mixture of 4-[4-azatricyclo(4.3.1.1$^{3,8}$)undecan-4-yl]-3-methyl-2,2-diphenylbutanenitrile and 4-[4-azatricyclo(4.3.1.1$^{3,8}$)-undecan-4-yl]-2,2-diphenylpentanenitrile as the residue.

B. To a solution of 280 parts of a mixture of 4-[4-azatricyclo(4.3.1.1$^{3,8}$)undecan-4-yl]-3-methyl-2,2-diphenylbutanenitrile and 4-[4-azatricyclo(4.3.1.1$^{3,8}$)-undecan-4-yl]-2,2-diphenylpentanenitrile in 950 parts of N,N-dimethylformamide is added 65 parts of sodium azide, 53 parts of ammonium chloride, and 1 part of lithium chloride. The resultant mixture is stirred at 90° for 9 hours, then chilled. Insoluble solids are filtered off, washed with N,N-dimethylformamide and then water, and finally dried in air. The product thus isolated is a mixture of 5-{3-[4-azatricyclo(4.3.1.1$^{3,8}$)undecan- 4-yl]-2-methyl-1,1-diphenylpropyl}-1H-tetrazole and 5-{3-[4-azatricyclo(4.3.1.1$^{3,8}$)undecan-4-yl]1,1-diphenylbutyl}-1H-tetrazole.

C. A solution consisting of 32 parts of a mixture of 5-{3-[4-azatricyclo(4.3.1.1$^{3,8}$-undecan-4-yl]-2-methyl-1,1-diphenylpropyl}-1H-tetrazole and 5-{3-[4-azatricyclo(4.3.1.1$^{3,8}$)undecan-4-yl]-1-diphenylbutyl}-1H-tetrazole, 140 parts of acetic anhydride, and 400 parts of pyridine is heated at the boiling point under reflux for 3 hours, then chilled. Approximately 100 parts of water is introduced; and the resultant mixture is stirred for 10 minutes, then stripped of solvent by vacuum distillation. The residue is partitioned between a saturated aqueous solution of sodium bicarbonate and ether. The ethereal phase is separated and consecutively washed with a saturated aqueous solution of sodium bicarbonate and water, then extracted with 2% hydrochloric acid. The acid extract is made alkaline, and the mixture thus obtained is extracted with ether. The ether extract is washed with water, dried over anhydrous sodium sulfate, and filtered. The filtrate is stripped of solvent by vacuum distillation, leaving a mixture of 2-{3-[4-azatricyclo(4.3.1.1$^{3,8}$)undecan-4-yl]-2-methyl-1,1-diphenylpropyl}-5-methyl-b 1,3,4-oxadiazole and 2-{3-[4-azatricyclo(4.3.1.1$^{3,8}$)-undecan-4-yl]-1,1-diphenylbutyl}-5-methyl-1,3,4-oxadiazole as the residue.

D. A solution of 1 part of a mixture of 2-{3-[4-azatricyclo(4.3.1.1$^{3,8}$)undecan-4-yl]-2-methyl-1,1-diphenylpropyl}-5-methyl-1,3,4-oxadiazole and 2-{3-[4-azatricyclo(4.3.1.1$^{3,8}$)undecan-4-yl]-1,1-diphenylbutyl}-5-methyl-1,3,4-oxadiazole in 20 parts of ether is acidified with a solution of hydrogen chloride in 2-propanol. The precipitate thrown down is filtered out, washed with ether, and dried in air. The product thus isolated is a mixture of 2-{3-[4-azatricyclo(4.3.1.1$^{3,8}$)undecan-4-yl]-2-methyl-1,1-diphenylpropyl}-5-methyl-,3,4-oxadiazole hydrochloride and 2-{3-[4-azatricyclo(4.3.1.1$^{3,8}$)undecan-4-yl]-1,1-diphenylbutyl}-5-methyl-1,3,4-oxadiazole hydrochloride melting in the range, 170°–190°, with gas evolution.

EXAMPLE 3

A. To a suspension of 62 parts of 5-{3-[4-azatricyclo(4.3.1.1$^{3,8}$)undecan-4-yl]-1,1-diphenylpropyl}-1H-tetrazole in 1000 parts of pyridine at −10° under nitrogen is added, with stirring during 10 minutes, 29 parts of ethyl oxalyl chloride. The resultant mixture is stirred for 10 minutes at −10°, then at 60°; for 1½ hours. Pyridine is thereupon stripped by vacuum distillation, and the residue is partitioned between aqueous 5% potassium carbonate and diethyl ether. The ethereal phase is washed well with water, dried over anhydrous sodium sulfate, and filtered. Removal of solvent from the filtrate by vacuum distillation affords ethyl 5-{3-[4-azatricyclo(4.3.1.1$^{3,8}$)-undecan-4-yl]-1,1-diphenylpropyl}-1,3,4-oxadiazole-2-carboxylate as the residue.

B. A solution of 10 parts of ethyl 5-{3-[4-azatricyclo(4.3.1.1$^{3,8}$)undecan-4-yl]-1,1-diphenylpropyl}-1,3,4-oxadiazole-2-carboxylate in a minimal amount of diethyl ether is acidified with a solution of hydrogen chloride in 2-propanol. The precipitate which forms is filtered off and recrystallized from a mixture of ethanol and ether to give ethyl 5-{3-[4-azatricyclo(4.3.1.1$^{3,8}$)-undecan-4-yl]-1,1-diphenylpropyl}-1,3,4-oxadiazole-2-carboxylate hydrochloride as yellow-green crystals melting at approximately 199°–200°.

C. A mixture of 5 parts of ethyl 5-{3-[4-azatricyclo(4.3.1.1$^{3,8}$)undecan-4-yl]-1,1-diphenylpropyl}-1,3,4-oxadiazole-2-carboxylate hydrochloride and 125 parts of aqueous 5% sodium hydroxide is heated at the boiling point under reflux for 5 minutes, then cooled and thereupon washed with diethyl ether. Sufficient hydrochloride acid is introduced to effect neutralization. The mixture thus obtained is extracted with dichloromethane. The extract is dried over anhydrous sodium sulfate and filtered. The filtrate is stripped of solvent by vacuum distillation; and the residue is purified by dissolving it in dichloromethane, washing the solution with water and thereupon drying it over anhydrous sodium sulfate, filtering and stripping the solvent from the filtrate via vacuum distillation, and finally recrystallizing the residue from a mixture of dichloromethane and ether. The product is further purified by washing it with ether, then drying it in air. The material thus isolated is 5-{3-[4-azatricyclo(4.3.1.1$^{3,81}$)-undecan-4-yl]-1,1-diphenylpropyl}-1,3,4-oxadiazole-2-carboxylic acid.

D. Upon heating 3 parts of 5-{3-[4-azatricyclo(4.3.1.1$^{3,8}$)undecan-4-yl]-1,1-diphenylpropyl}-1,3,4-oxadiazole-2-carboxylic acid at 145°–150° for 15 minutes, the solid melts and gas is evolved. The resultant material is chilled, forming a glass, which is taken up in diethyl ether. The ether solution is filtered, and the filtrate is stripped of solvent by distillation. The residue is 2-{3-[4-azatricyclo(4.3.1.1$^{3,8}$)undecan-4-yl]-1,1-diphenylpropyl}-1,3,4-oxadiazole.

EXAMPLE 4

A. Substitution of 21 parts of 4-(3-chloropropyl)-4-azatricyclo[4.3.1.1$^{3,8}$]undecane [preparable from the corresponding hydrochloride (U.S. Pat. No. 3,845,038 as hereinbefore described] for the 4-(2chloroethyl)-4-azatricyclo[4.3.1.1$^{3,8}$]undecane called for in Example 1A affords, by the procedure there detailed, 5-[4-azatricyclo(4.3.1.1$^{3,8}$)undecan-4-yl]2,2-diphenylpentanenitrile.

B. Substitution of 251 parts of 5-[4-azatricyclo(4.3.1.1$^{3,8}$)undecan-4-yl]-2,2-diphenylpentanenitrile for the 4-[4-azatricyclo(4.3.1.1$^{3,8}$)undecan-4-yl]-2,2-diphenylbutanenitrile called for in Example 1C affords, by the procedure there detailed, 5-{4-[4-azatricyclo(4.3.1.1$^{3,8}$)undecan-4-yl]-1,1-diphenylbutyl}-1H-tetrazole.

C. Substitution of 49 parts of 5-{4-[4-azatricyclo(4.3.1.1$^{3,8}$)undecan-4-yl]-1,1-diphenylbutyl}-1H-tetrazole for the 5-{3-[4-azatricyclo(4.3.1.1$^{3,8}$)undecan-4-yl]-1,1-dephenylpropyl}-1H-tetrazole called for in Example 1E affords, by the procedure there detailed, 2{-4-[4-azatricyclo(4.3.1.1$^{3,8}$)undecan-4-yl]-1,1-diphenylbutyl}-5-methyl-1,3,4-oxadiazole.

EXAMPLE 5

Substitution of 180 parts of 2-methylpropanoic acid anhydride for the acetic anhydride called for in Example 1E affords, by the procedure there detailed, 2-{3-[4-azatricyclo(4.3.1.1$^{3,8}$)undecan-4-yl]-1,1-diphenylpropyl}-5-(1-methylethyl)-1,3,4-oxadiazole.

EXAMPLE 6

A. To a solution of approximately 59 parts of α-(2-pyridinyl)benzeneacetonitrile in 135 parts of toluene is added, with stirring under nitrogen, 13 parts of a 57% dispersion of sodium hydride in oil. The resultant mixture is heated to 100° and stirred thereat under nitrogen for 1 hour. The greenish-yellow suspension which eventuates is cooled to around 60°, at which temperature a solution of 64 parts of 4-(2-chloroethyl)-4-azatricyclo [4.3.1.1.$^{3,8}$]undecane in 450 parts of toluene is introduced with stirring, during 20 minutes. The resultant mixture is stirred at 100° for 1 hour, then for 1 hour longer while cooling to room temperature. At this point, 10 parts of water is stirred in, the aqueous and organic phases are separated, the aqueous phase is extracted with toluene and then discarded, and the extract and organic phase are combined and thereupon consecutively washed with water, dried over anhydrous sodium sulfate, and filtered. The filtrate is acidified with a solution of hydrogen chloride in 2-propanol. The precipitate which forms is filtered off and taken up on 10 volumes of water. The resultant solution is made alkaline with aqueous 15% sodium carbonate. The mixture so produced is extracted with diethyl ether. The ether solution is dried over anhydrous sodium sulfate and stripped of solvent by distillation, affording an orange oil. The oil is dissolved in a solution of 27 parts of oxalic acid in 2500 parts of water. Upon removal of water by vacuum distillation, there remains as the residue a gummy material which solidifies on trituration with a 1:1 mixture of diethyl ether and toluene. The solid is filtered out and partitioned between an aqueous 10% solution of sodium carbonate and diethyl ether. The ethereal phase is separated, dried over anhydrous sodium sulfate, filtered, and stripped of solvent by vacuum distillation. The residue is taken up in pentane, and the pentane solution is mixed with decolorizing charcoal and filtered. The filtrate is stripped of solvent by vacuum distillation, and the residue thus obtained is dissolved in 400 parts of absolute ethanol. To the ethanol solution is added a solution of 16 parts of oxalic acid in 80 parts of absolute ethanol. The crystalline precipitate which forms is filtered and taken up in a minimum quantity of water. The resultant solution is made alkaline with aqueous 15% sodium carbonate, and the mixture so produced is extracted with diethyl ether. The ether extract is washed with water, dried over anhydrous sodium sulfate, and stripped of solvent by vacuum distillation, affording 4-[4-azatricyclo(4.3.1.1$^{3,8}$)undecan-4-yl]-2-phenyl-2-(2-pyridinyl)-butanenitrile as the residue, a pale yellow gum.

B. A mixture of 405 parts of 4-[4-azatricyclo(4.3.1.1$^{328}$)undecan-4-yl]-2-phenyl-2-(2-pyridinyl)-butanenitrile, 98 parts of sodium azide, 81 parts of ammonium chloride, 3 parts of lithium chloride, and 7500 parts of N,N-dimethylformamide is stirred at 125° for 10½ hours under nitrogen, then chilled. The precipitate which forms is filtered off and extracted with N,N-dimethylformamide, the filtrate and extract are combined, and the resultant solution is stripped of solvent by vacuum distillation. The residual tan oil is washed by decantation with ether, then taken up in 15 l of aqueous 0.4% sodium hydroxide. The solution thus obtained is mixed with diatomaceous earth. The mixture is filtered, and the filtrate is neutralized with 0.5% hydrochloric acid. The gummy precipitate which forms is 5-{3-[4-azatricyclo(4.3.1.1$^{3,8}$)undecan-4-yl]-1-phenyl-1-(2-pyridinyl)propyl}-1H-tetrazole, which is isolated by filtration and dried in air.

C. A solution of 9 parts of 5-{3-[4-azatricyclo(4.3.1.1$^{3,8}$)undecan-4-yl]-1-phenyl-1-(2-pyridinyl)propyl}-1-H-tetrazole and 20 parts of acetic anhydride in 100 parts of pyridine is heated at the boiling point for 1 hour. Liquids are removed by vacuum distillation, and the residue is partitioned between aqueous 10% sodium carbonate and diethyl ether. The ethereal phase is separated, washed with water, dried over anhydrous sodium sulfate, and stripped of solvent by vacuum distillation. The residue is 2-{3-[4-azatricyclo(4.3.1.1$^{3,8}$)undecan-4-yl]-1-phenyl-1-(2-pyridinyl)-propyl}-5-methyl-,3,4-oxadiazole.

D. A solution of 1 part of 5-{3-[4-azatricyclo(4.3.1.1$^{3,8}$)undecan-4-yl]-1-phenyl-1-(2-pyridinyl)propyl}-5-methyl- 1,3,4-oxadiazole in 20 parts of diethyl ether is acidified with a solution of hydrogen chloride in 2-propanol. The precipitate which forms is isolated by filtration and dried in air. The product thus obtained is 2-{3-[4-azatricyclo(4.3.1.1$^{3,8}$)undecan-4-yl]-1-phenyl-1-(2-pyridinyl)-propyl}-5-methyl-1,3,4-oxadiazole hydrochloride hemihydrate. Water of crystallization can be removed by warming the product in vacuo.

EXAMPLE 7

A. Substitution of 59 parts of α-(3-pyridinyl)-benzeneacetronitrile for the α-(2-pyridinyl)benzeneacetonitrile called for in Example 6A affords, by the procedure there detailed, 4-[4-azatricyclo(4.3.1.1$^{3,8}$)undecan-4-yl]-2-phenyl-2-(3-pyridinyl)-butanenitrile.

B. Substitution of 405 parts of 4-[4-azatricyclo(4.3.1.1$^{3,8}$)undecan-4-yl]-2-phenyl-2-(3-pyridinyl)-butanenitrile for the 4-[4-azatricyclo(4.3.1.1$^{3,8}$)undecan-4-yl]-2-phenyl-2-(2-pyridinyl)butanenitrile called for in Example 6B affords, by the procedure there detailed, 5-{3-[4-azatricyclo(4.3.1.1$^{3,8}$)undecan-4-yl]-1-phenyl-1-(3-pyridinyl)-propyl}-1H-tetrazole.

C. Substitution of 9 parts of 5-{3-[4-azatricyclo(4.3.1.1$^{3,8}$)undecan-4-yl]-1-phenyl-1-(3-pyridinyl)propyl}-1H-tetrazole for the 5-{3-[4-azatricyclo(4.3.1.1$^{3,8}$)undecan-4yl]-1-phenyl-1-(2-pyridinyl)propyl}-1H-tetrazole called for in Example 6C affords, by the procedure there detailed, 2-{3-[4-azatricyclo(4.3.1.1$^{3,8}$)undecan-4-yl]-1-phenyl-1-(3-pyridinyl)propyl}-5-methyl-1,3,4-oxadiazole.

What is claimed is:

1. A compound of the formula

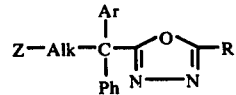

wherein R represents hydrogen or lower alkyl, Ar represents phenyl or pyridyl, Ph represents phenyl, Alk represents alkylene containing more than 1 and fewer than 4 carbons, and Z represents 4-azatricyclo[4.3.1.1$^{3,8}$]undecan-4-yl.

2. A compound according to claim 1 which is 2-{3-[4-azatricyclo(4.3.1.1$^{3,8}$)undecan-4-yl]-1,1-diphenyl-propyl}-5-methyl-1,3,4-oxadiazole.

3. A compound according to claim 1 which is 2-{3-[4-azatricyclo(4.3.1.1$^{3,8}$)undecan-4-yl]-1,1-diphenyl-propyl}-1,3,4-oxadiazole.

4. A compound according to claim 1 having the formula

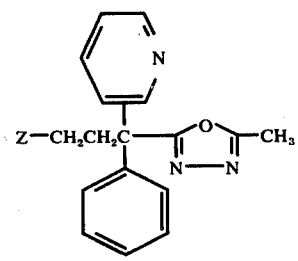
wherein Z represents 4-azatricyclo[4.3.1.1$^{3,8}$]undecan-4-yl.
5. A compound according to claim 1 which is 2-{3-[4-azatricyclo(4.3.1.1$^{3,8}$)undecan-4-yl]-1-phenyl-1-(2-pyridinyl)propyl}-5-methyl-1,3,4-oxadiazole.
* * * * *

UNITED STATES PATENT AND TRADEMARK OFFICE
CERTIFICATE OF CORRECTION

PATENT NO. : 4025524
DATED : May 24, 1977
INVENTOR(S) : Gilbert W. Adelstein & H. William Sause It is certified that error appears in the above-identified patent and that said Letters Patent are hereby corrected as shown below:

Column 1, line 57, "3-propanediyl" should read -- 1,3-propanediyl --.

Column 2, line 55, "presence control" should read -- presence of compound is not more than 25% of the mean control --.

Column 3, line 55, "intervals until" should read -- intervals, and the drug dose is repeated at 15-minute intervals until --.

Column 4, line 11, "o-mcgm" should read -- 10 mcgm --.

Column 5, line 9, "number" should read -- numbers --.

Column 5, line 65, "(alky-co)$_2$O" should read -- (alkyl-CO)$_2$O --.

Column 7, line 5, "4.2,1.1$^{3,8}$" should read -- 4.3,1.1$^{3,8}$ --.

Column 8, line 35, "oxadiazone" should read -- oxadiazole --.

Column 9, line 24, "methyl-b" should read -- methyl --.

UNITED STATES PATENT AND TRADEMARK OFFICE
CERTIFICATE OF CORRECTION

PATENT NO. : 4025524
DATED : May 24, 1977
INVENTOR(S) : Gilbert W. Adelstein & H. William Sause It is certified that error appears in the above-identified patent and that said Letters Patent are hereby corrected as shown below:

Column 9, line 39, "methyl-,3,4" should read -- methyl-1,3,4 --.

Column 10, line 7, "hydrochloride" should read -- hydrochloric --.

Column 10, line 19, "4.3.1.1$^{3,81}$" should read -- 4.3.1.1$^{3,8}$ --.

Column 11, line 15, "on" should read -- in --.

Column 11, line 47, "4.3.1.1$^{328}$" should read -- 4.3.1.1$^{3,8}$ --.

Column 12, line 8, "methyl-,3.4" should read -- methyl-1,3,4 --.

Column 12, lines 23 & 24, "benzeneacetronitrile" should read -- benzeneacetonitrile --.

Signed and Sealed this

Eleventh Day of April 1978

[SEAL]

Attest:

RUTH C. MASON
Attesting Officer

LUTRELLE F. PARKER
Acting Commissioner of Patents and Trademarks